United States Patent [19]

Veber et al.

[11] Patent Number: 4,493,934

[45] Date of Patent: Jan. 15, 1985

[54] 2(3-AMINO-2-OXOPYRROLIDIN-1-YL) ACETIC ACID AND N-ACYLATED DERIVATIVES THEREOF

[75] Inventors: Daniel F. Veber, Ambler; Roger M. Freidinger, Hatfield, both of Pa.

[73] Assignee: Merck & Co., Inc., Rahway, N.J.

[21] Appl. No.: 421,594

[22] Filed: Sep. 22, 1982

Related U.S. Application Data

[62] Division of Ser. No. 80,844, Oct. 1, 1979, Pat. No. 4,377,515.

[51] Int. Cl.$^3$ .................................... C07D 207/273
[52] U.S. Cl. .................................................. 548/550
[58] Field of Search ...................................... 548/550

[56] References Cited

U.S. PATENT DOCUMENTS 3,714,175  1/1983  Shigezane et al. ................. 548/550

Primary Examiner—Glennon H. Hollrah
Assistant Examiner—D. B. Springer
Attorney, Agent, or Firm—Thomas E. Arther; Raymond M. Speer

[57] ABSTRACT

Novel peptides of the formula:

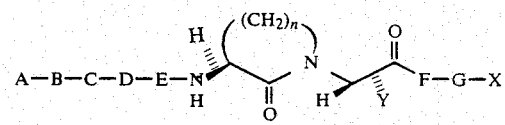

where A through G, X and Y are various amino acids and substituents; having long lasting LHRH agonist and antagonist activity; useful in promoting fertility, reducing fertility, respectively.

3 Claims, No Drawings

2(3-AMINO-2-OXOPYRROLIDIN-1-YL) ACETIC ACID AND N-ACYLATED DERIVATIVES THEREOF

This is a division of application Ser. No. 80,844, filed Oct. 1, 1979 now U.S. Pat. No. 4,377,515, issued 03/22/83.

BACKGROUND OF THE INVENTION

1. Field of the Invention

The present invention is concerned with novel peptide compounds having long lasting LHRH agonist and antagonist activity and with pharmaceutical compositions containing said novel peptide compounds, as well as their use in methods of promoting and methods of reducing fertility.

2. Brief Description of the Prior Art

Luteinizing hormone-releasing hormone (LHRH) is a neurohumoral hormone produced in the hypothalamus which stimulates the secretion of the pituitary hormones, luteinizing hormone (LH) and follicle-stimulating hormone (FSH), which in turn produce changes resulting in the induction of ovulation. LHRH has the following structure:

pyroGlu—His—Trp—Ser—Tyr—Gly—Leu—Arg—Pro—GlyNH$_2$

Synthetic replicates of LHRH were readily available shortly after the primary sequence was disclosed in 1971 and, as a result, a sizable number of structural analogs of LHRH have been made and tested over the last few years. Some of these have proved to be more potent than LHRH as well as long-acting. See Rivier et al., Peptides 1976 (Proceedings of the Fourteenth European Peptide Symposium, Wépion, Belgium, April 11–17, 1976), pp. 427–436. Thus, a D-amino acid has been utilized in the 6-position and/or N-methyl-Leu$^7$ substitution has been made in order to obtain potent, long-acting LHRH agonists and antagonists. These prior studies have also indicated the importance of the backbone conformation to full potency of the analogs.

The novel peptides of the present invention, in contrast to the prior art, possess a five- or six- membered lactam bridge between the 6- and 7- positions of the peptide. It is theorized that this novel structure improves the biologically active (receptor bound) conformation of the peptide, thus affording greater potency, as well as the resistance of the peptide to enzyme degradation, thus extending the useful life of the peptide.

The novel peptides of the present invention are prepared in accordance with a novel process. Cyclizations of methionine sulfonium salts which have been previously reported have resulted in O-, rather than N-alkylation. See Yeung, et al., Biochemistry, Vol. 16, p. 1635 (1977).

SUMMARY OF THE INVENTION

The present invention concerns novel peptides of the formula:

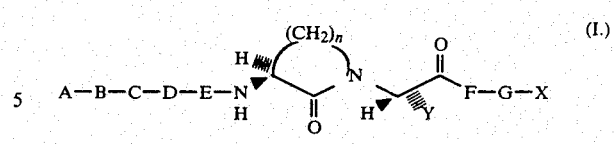

wherein, unless otherwise indicated, an amino or imino acid has the "L-" stereoconfiguration:

A is L- or D-pyroGlu (pyroglutamic acid residue): L- or D- N-acetyl or N-pyroGlu imino acid; acetyl D-Phe (Phenylalanine); or C$_{3-7}$ cycloalkyl acyl;

B is His (Histidine); Gly(Glycine); L- or D- aromatic or aliphatic amino acid; or is absent;

C is L- or D- aromatic or aliphatic amino acid;

D is Ser (Serine; Thr (Threonine); or Ala (Alanine;

E is aromatic amino acid;

F is amino acid with a basic side chain;

G is imino acid or aliphatic amino acid;

X is GlyNH$_2$ (Glycineamido); AlaNH$_2$ (Alanineamido); aminoethyl; aminopropyl; or aminohydroxyethyl;

Y is hydrogen or C$_{1-14}$ alkyl; and n is 2 or 3.

Preferred novel agonist peptides of the present invention are:

PyroGlu-His-Trp-Ser-Tyr-6,7-[2-(S-3-amino-2-oxo-pyrrolidin1yl)-S-2-isopropylmethylacetic acid]-Arg-Pro-GlyNH$_2$ PyroGlu-His-Trp-Ser-Tyr-6,7-[2-(S-3-amino-2-oxo-pyrrolidin1yl)-S-2-isopropylmethylacetic acid]-Arg-Pro-ethylamide Preferred novel antagonist peptides of the present invention are:

PyroGlu-D-Phe-Trp-Ser-Tyr-6,7-[2-(S-3-amino-2-oxo-pyrrolidin-1-yl)-S-2-isopropylmethylacetic acid]-Arg-Pro-GlyNH$_2$ N-acetyl-Pro-D-Phe-D-Trp-Ser-Tyr-6,7-[2-(S-3-amino-2-oxo-pyrrolidin-1-yl)-S-2-isopropylmethylacetic acid]-Arg-Pro-GlyNH$_2$ For agonist activity, the A substituent is the same as that for endogenous LHRH, that is pyroGlu (pyroglutamic acid residue). For antagonist activity, the A substituent is L- or D- pyroGlu; L- or D- N-acetyl imino acid, preferably N-acetyl Pro (Proline) or N-acetyl Hyp (Hydroxyproline); L- or D- N-pyroGlu imino acid, preferably N-pyroGlu-Pro or N-pyroGlu-Hyp; acetyl D-Phe; or C$_{3-7}$ cycloalkyl acyl, for example cyclopropylcarbonyl.

For agonist activity, the B substituent is the same as that for endogeneous LHRH, that is, His. For antagonist activity, the B substituent is Gly; and L- or D- aromatic amino acid, preferably a member selected from the group consisting of Phe, Trp (Tryptophan), Tyr (Tyrosine), and His; an L- or D- aliphatic amino acid, preferably a member selected from the group consisting of Ala, Leu (Leucine), Ile (Isoleucine), and Val (Valine); or is absent altogether.

For agonist activity, the C substituent is an aromatic amino acid, preferably a member selected from the group consisting of Phe, Trp, Tyr, and His. For antagonist activity, the C substituent is an L- or D-aromatic or aliphatic amino acid, as described above for substituent B.

For both agonist and antagonist activity, the D substituent is Ser, Thr, or Ala.

For both agonist and antagonist activity, the E substituent is an aromatic amino acid, as described above for substituent C.

For both agonist and antagonist activity, the F substituent is an amino acid with a basic side chain, preferably a member selected from the group consisting of Lys (Lysine), Arg (Arginine), and Orn (Ornithine).

For both agonist and antagonist activity, the G substituent, is an imino acid, preferably Pro or Hyp; or an aliphatic amino acid, as described above for substituent B.

For both agonist and antagonist activity, the X substituent is $GlyNH_2$, $AlaNH_2$, aminoethyl ($-NHCH_2CH_3$), aminopropyl [$-NH(CH_2)_2CH_3$], or aminohydroxyethyl [$-NH(CH_2)_2OH$]. Thus, the X substituent is an amide end group which may be an amino acid, in which case the novel peptide is a decapeptide, or a fragment, in which case the novel peptide is a nonapeptide.

For both agonist and antagonist activity, substituent Y is hydrogen or $C_{1-4}$ alkyl, preferably isopropylmethyl.

The novel peptides of the present invention have as an essential feature a lactam dipeptide conformation constraining bridge between the α-carbon of $Gly^6$ and the amino group of $Leu^7$ of the LHRH peptide. This lactam bridge is further illustrated in the following partial formulas from LHRH and a novel peptide of the present invention:

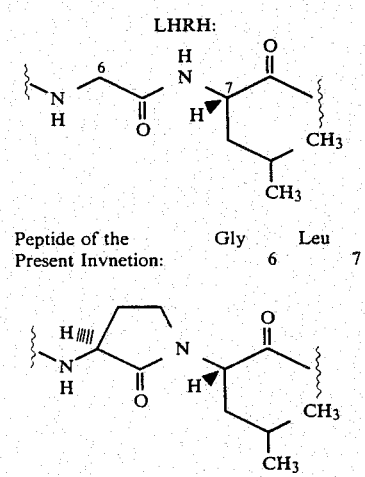

In accordance with the present invention there is provided a method of promoting fertility, comprising administering to a patient in need of such treatment, a therapeutically effective amount of a peptide of the formula:

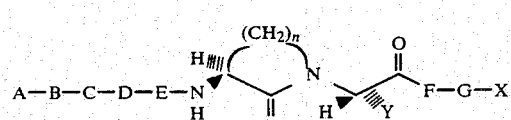

(I.)

wherein:
A is pyroGlu;
B is His;

C is aromatic amino acid, preferably a member selected from the group consisting of Phe, Trp, Tyr, and His;
D is Ser, Thr, or Ala;
E is aromatic amino acid, preferably a member selected from the group consisting of Phe, Trp, Tyr, and His;
F is amino acid with a basic side chain, preferably a member selected from the group consisting of Lys, Arg, and Orn;
G is imino acid, preferably a member selected from the group consisting of Pro and Hyp, or aliphatic amino acid, preferably a member selected from the group consisting of Ala, Leu, Ile, and Val;
X is $GlyNH_2$, $AlaNH_2$, aminoethyl, aminopropyl, or aminohydroxyethyl;
Y is hydrogen or $C_{1-4}$ alkyl, preferably isopropylmethyl; and
n is 2 or 3.

Dosage levels of the order of 60 μg. to 35 mg. per day are useful in the treatment of the above-indicated conditions. For example, fertility is promoted by the administration of from about 1 μg. to 0.5 milligrams of the peptide per kilogram of body weight per day. Advantageously, from about 1 μg. to about 300 μg. per kilogram of a body weight, and especially from about 2 μg. to about 100 μg./kg. per daily dosage produces highly effective results.

For convenience, the novel peptides of the present invention have been divided into LHRH agonist and antagonist peptides with respect to their activity in controlling fertility, the agonist peptides promoting fertility and the antagonist peptides reducing fertility. In fact, however, while the antagonist peptides will only reduce fertility, the fertility controlling activity of the agonist peptides is dosage dependent. As indicated above, dosage levels of the order of 60 μg. to 35 mg. per day are useful in promoting fertility. On the other hand, dosage levels of the order of 0.5 mg. to 500 mg. per day are useful in reducing fertility. Thus, fertility is reduced by administration of from about 10 μg. to about 7.5 mg. of the peptide per Kilogram of body weight per day. Advantageously, from about 0.02 mg. to about 2 mg. per kilogram of body weight, and especially from about 0.03 mg. to about 1.0 mg./kg. per daily dosage produces highly effective results.

In accordance with the present invention there is also provided a method of reducing fertility comprising administering to a patient in need of such treatment, a therapeutically effective amount of a peptide of the formula:

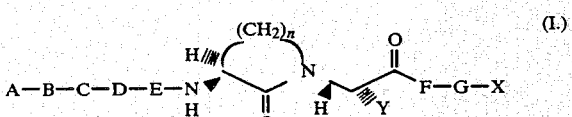

(I.)

wherein:
A is L- or D- pyroGlu; L- or D- N-acetyl or N-pyroGlu imino acid, preferably a member selected from the group consisting of N-acetyl Pro, N-acetyl Hyp, N-pyro-Glu Pro, and N-pyroGlu Hyp; acetyl D-Phe; or $C_{3-7}$ cycloalkyl acyl, preferably cyclopropylcarbonyl;
B is Gly; L- or D- aromatic amino acid, preferably a member selected from the group consisting of Phe, Trp, Tyr, and His; an L- or D- aliphatic amino acid, preferably a member selected from the group consisting of Ala, Leu, Ile, and Val; or is absent altogether;

C is L- or D- aromatic or aliphatic amino acid, as described above for substituent B;

D is Ser, Thr, or Ala;

E is aromatic amino acid, as described above for substituent B;

F is amino acid with a basic side chain, preferably a member selected from the group consisting of Lys, Arg, and Orn;

G is imino acid, preferably a member selected from the group consisting of Pro and Hyp; or aliphatic amino acid, as described above for substituent B;

X is $GlyNH_2$, $AlaNH_2$, aminoethyl, aminopropyl, or aminohydroxyethyl;

Y is hydrogen or $C_{1-4}$ alkyl, preferably isopropylmethyl; and n is 2 or 3.

Dosage levels of the order of 0.5 mg. to 500 mg. per day are useful in the treatment of the above indicated conditions. For example, fertility is reduced by the administration of from about 10 μg. to about 7.5 mg. of the peptide per kilogram of body weight per day. Advantageously, from about 0.02 mg. to about 2 mg. per kilogram of body weight and especially from about 0.03 mg. to about 1 mg./kg. per daily dosage produce highly effective results.

The amount of active ingredient that may be combined with the carrier materials to produce a single dosage form will vary depending upon the host treated and the particular mode of administration. For example, a formulation intended for the oral administration of humans may contain from 5 mg. to 1 gram of active agent compounded with an appropriate and convenient amount of carrier material which may vary from about 5 to about 95 percent of the total composition. Dosage unit forms will generally contain between from about 25 mg. to about 500 mg. of active ingredient.

It will be understood, however, that the specific dose level for any particular patient will depend upon a variety of factors including the activity of the specific compound employed, the age, body weight, general health, sex, diet, time of administration, route of administration, rate of excretion, and drug combination.

In accordance with the present invention there is further provided pharmaceutical compositions for use in promoting fertility, and in reducing fertility. The novel peptides of the present invention possess a high degree of LHRH agonist and antagonist activity and are long-acting.

For these purposes the novel peptides of the present invention may be administered orally, topically, parenterally, by inhalation spray, intravaginally, or rectally in dosage unit formulations containing conventional non-toxic pharmacetically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the peptides of the present invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example, starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethyl-cellulose, methyl-cellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acid anhydrides and hexitol, for example polyoxyethylene sorbitan mono-oleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspension may contain a thickening agent, for example beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acid anhydrides and hexitol, for example sorbitan mono-oleate, and condensation products of the said partial esters with ethylene oxide, for example polyoxyethylene sorbitan mono-oleate. The emulsions may also contain sweetening and flavouring agents.

Syrups and elixirs may be formulated with sweetening agents, for example glycerol, sorbitol or sucrose. Such formulations may also contain a demulcent, a preservative and flavouring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may be also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The peptides of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are coca butter and polyethylene glycols.

The novel peptides of the present invention, with respect to the various amino acid substituents of the peptide, are prepared in accordance with well-known methods in the art for the synthesis of peptides. However, the unique lactam dipeptide bridge in the novel peptides of the present invention is prepared in accordance with a novel process, with which, accordingly, the present invention is also concerned. The novel preparation method of the present invention may be illustrated by the following diagram:

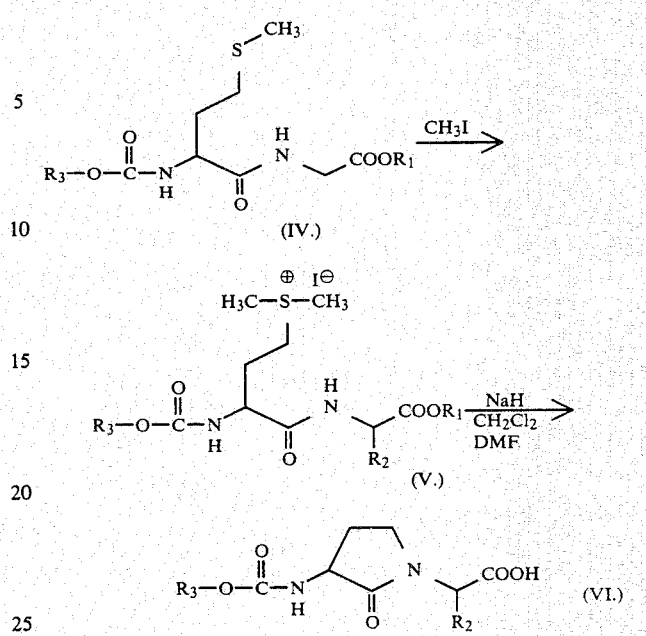

$R_1$ is a $C_{1-4}$ alkyl group, preferably methyl; $R_2$ is the same as Y, defined above; and $R_3$ is $C_{1-12}$ alkyl, for example t-butyl, $C_{1-4}$ ar or alkyl, for example, benzyl. The

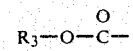

group is a protective group, and may be, for example butyloxycarbonyl (BOC).

An additional feature, and unexpected advantage of the novel process of the present invention is conversion of most of the alkyl ester ($COOR_1$) to the carboxylic acid during the course of the reaction without the requirement of any additional treatment step. Separation of the acid product or, alternatively, hydrolysis of the small amount of ester product to acid may be carried out.

In the first step of the preparation method, there may be used as the starting material, for example, the methyl ester of BOC protected dipeptide Met-Leu (Methionine-Leucine). This starting material would thus be the compound of Formula IV. where $R_1$ is methyl, $R_2$ is isopropylmethyl, and $R_3$ is t-butyl.

The starting material is treated with an alkylating agent, for example dimethylsulfate, diethylsulfate, methylfluorosulfonate, methyl trifluoromethanesulfonate, trimethyloxonium fluoroborate, preferably methyl iodide, which, in the case of methyl iodide, may also serve as the solvent medium for the reaction. However, any suitable anhydrous aprotic solvent can be used. A temperature of from 0° C. to 40° C. may be employed. Preferably, the starting material is treated with methyl iodide by admixing and stirring at room temperature for about two days. The resulting product is the sulfonium salt of the alkyl ester of protected-Met-Leu, illustrated by Formula V.

In the second step of the preparation method of the present invention, the sulfonium salt of Formula V. is treated with a strong base in order to effect ring closure. The strong base may be an alkali metal hydride, preferably sodium hydride, but may also be, for example, lithium diisopropylamide or potassium t-butoxide. The reaction is carried out in an anhydrous aprotic solvent, for example methylene chloride and dimethylformamide (DMF), either separately or combined; alkyl ethers, for example dimethoxyethane; or tetrahydrofuran. The reaction temperature is preferably about 0° C., but temperatures of −50° C. to 50° C. are suitable.

The resulting product is a protected 2-(3-amino-2-oxopyrrolidin-1-yl) acetic acid which may be 2-alkyl substituted. This product is illustrated by Formula VI. and is a novel compound, as is the corresponding unprotected compound, which may be prepared by removing the protecting group through cleavage, for example by treatment with a strong acid or catalytic hydrogenation. Consequently, the present invention is also concerned with the following novel compounds:

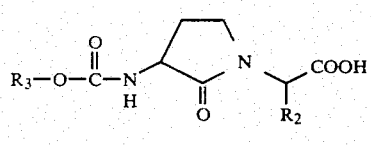
(VI.)

and

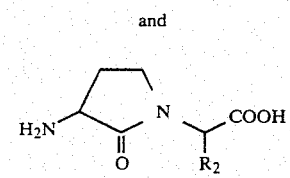
(VII.)

where $R_2$ is $C_{1-4}$ alkyl and $R_3$ is $C_{1-12}$ alkyl or $C_{1-4}$ aralkyl.

Thus, the novel method of preparation of the present invention is a method of preparing a compound of the formula:

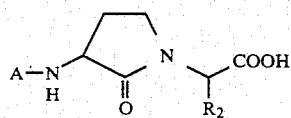
(VIII.)

where A is hydrogen or

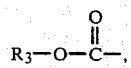

comprising the steps of
(1) treating a

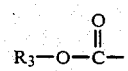

protected Met-aliphatic amino acid ester of the formula

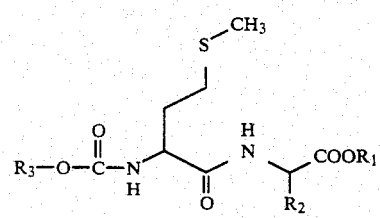
(IV.)

with an alkylating agent, whereby the corresponding sulfonium salt is produced; and (2) treating the sulfonium salt prepared in Step (1) with a strong base in order to effect ring closure and prepare the compound of Formula VIII. where A is

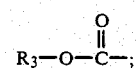

and
(3) cleaving the

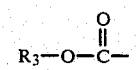

protecting group from the compound of Formula VI. to prepare the compound of formula VIII. where A is hydrogen.

The following example illustrates preparation of a novel peptide of the present invention.

EXAMPLE

PyroGlu-His-Trp-Ser-Tyr-6,7-[2-(S-3-Amino-2-Oxo-Pyrrolidin-1-yl)-S-2- Isopropylmethylacetic Acid]-Arg-Pro-GlyNH₂

A. BOC-L-Met-L-Leu-OMe 6.225 g. (25 mole) of BOC-L-Met was dissolved in 160 ml. of degassed dimethylformamide and cooled under nitrogen to 0° C. 4.55 g. (25 mmole) of L-Leu-OMe was dissolved in 80 ml. of dimethylformamide and set aside. To the BOC-L-Met was added 5.38 ml. of diphenylphosphorylazide in 10% excess followed by 3.48 ml. of triethylamine in 10% excess, followed by the L-Leu-OMe. The reaction mixture was stirred at 0° C. for 3 hrs., then at room temperature for 16 hrs. The solution was concentrated and treated with 3:1 dimethylformamide/ water and mixed bed resin, whereupon it crystallized out on the resin. The resin and crystals were filtered and the resin washed with dimethylformamide to isolate the product. The filtrate was then concentrated and recrystallized from ethyl acetate/hexane. 7.74 g. of product was obtained.

B. Sulfonium Salt of BOC-L-Met-L-Leu-OMe 7 g. (0.019 mole) of the ester product of A above was dissolved in 40 ml. of neat methyl iodide and stirred at room temperature for 1 hr. The reaction mixture was concentrated by water aspiration and in vacuo drying, and the residue was washed by evaporating with dichloromethane and methanol to form a foam in 90% yield (9.13 g.)

C. Cyclization to form BOC-[2-(S-3-Amino-2-Oxo-Pyrrolidin-1-yl)-S-2-Isopropylmethylacetic Acid].

The sulfonium salt product of B. above (9.13 g.) was dissolved in 300 ml. of a 1:1 mixture of dimethylformamide and dichloromethane and cooled to 0° C. under nitrogen. Two equivalents (1.5 g.) of a 50% dispersion of sodium hydride in mineral oil was added in one portion. After 2 hrs. 100 ml. of methyl acetate was added and this was followed by 2 ml. of water to quench the reaction, after which the reaction mixture was allowed to stand overnight. The reaction mixture was partitioned between dichloromethane and water, and the water was acidified to pH 4 with concentrated citric acid and extracted three times with dichloromethane. The dichloromethane portion was dried over sodium sulfate and concentrated to a crystalline mass. Two crops of crystals totaled 2.214 g. The product is BOC-blocked 2-(3-amino-2-oxo-pyrrolindin -1-yl)-2-isopropylmethyl acetic acid.

D. BOC-[2-(S-3-Amino-2-Oxo-Pyrrolidin-1-yl)-S-2-Isopropylmethylacetic Acid]-Arg-Pro-GlyNh$_2$ 1.6 g. (5 mmole) of the 2-(3-amino-2-oxo-pyrrolidin-1-yl)-2-isopropylmethyl acetic acid prepared in C. above was dissolved in 35 ml. of degassed dimethylformamide and cooled to 0° C. under nitrogen. 9.5 mmole of the TPA (trifluoroacetic acid)salt of H-Arg-Pro-GlyNh$_2$, previously prepared by methods known in the art, was dissolved in 15 ml. of degassed dimethylformamide, cooled, and set aside. To the acid solution was added 1.097 ml. (5.5 mmole) of diphenylphosphorylazide and 0.697 ml. (5.5 mmole) of triethylamine, followed by the pre-cooled peptide solution. The reaction mixture was stirred at 0° C. for 3 hrs., then at room temperature overnight. Product work-up involved a silica gel filtration with 70:30:3 chloroform/methanol/ aqueous ammonia. A foam product (2.5 g.) was obtained.

E. Deblocking of BOc[2-(S-3-Amino-2-Oxo-Pyrrolidin-1-yl)-S-2-Isopropylmethylacetic Acid]-Arg-Pro-GlyNh$_2$ The peptide product of D. above was used as a foam and dissolved in 30 ml. of trifluoroacetic acid containing 1% ethanedithiol (EDT) at 0° C., after which it was stirred at room temperature for 15 min., followed by solvent removal. Pumping and washing with ether removed most of the EDT. A foam product (2.77 g.) was obtained.

F. PyroGlu-His-Trp-Ser-Tyr-6,7-[2-(S-3-Amino-2-oxo-Pyrrolidin-1-yl)-S-2-Isopropylmethlacetic Acid]-Arg-Pro-GlyNh$_2$ 950 mg. (1.3 mmole) of the hydrazide PyroGlu-His-Trp-Ser-Tyr-NHNH$_2$, previously prepared by methods known in the art, was dissolved in 13 ml. of degassed dimethylformamide and cooled to −10° C. under nitrogen in a 1:1 methanol/water dry ice bath. There was then added 5 equivalents (6.5 mmole) of 5.8 M hydrochloric acid/tetrahydrofuran (1.2 ml.). The reaction mixture was cooled to −25° C. and there was added a 1:19 solution of isoamylnitrite/dimethylformamide until a positive starch/KI test reaction was obtained. About 8 ml. of solution was required. Then layer chromatography showed no hydrazide remained. The reaction mixture was cooled to −40° C. and the peptide product of E. above, cooled and dissolved in 2 ml. of dimethylformamide, was added. The ph was raised to 8 with triethylamine. The reaction mixture was stored at −20° C. for 24 hrs., after which the pH was readjusted. Additional peptide was added, but after 24 hrs. there was no change in the thin layer chromatography of the product. The product was concentrated in vacuo, dissolved in butanol, and partitioned with water. The butanol layer was placed on a silica gel column and eluted with 10:5:1:3 ethyl acetate/pyridine/acetic acid/water. The fractions were collected and concentrated, then precipitated with chloroform/hexane to give 150 mg. of final product.

What is claimed is:

1. A compound of the formula:

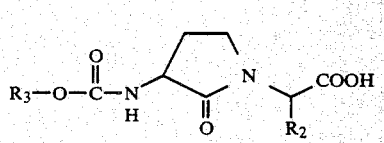

wherein:
R$_2$ is C$_{1-4}$ alkyl; and
R$_3$ is C$_{1-12}$ alkyl; or C$_{1-4}$ aralkyl.

2. A compound of the formula:

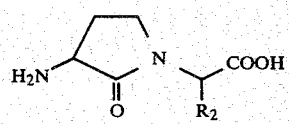

wherein
R$_2$ is C$_{1-4}$ alkyl.

3. The compound of claim 2 wherein R$_2$ is isopropyl methyl.

* * * * *